United States Patent
Yamazaki et al.

(10) Patent No.: US 7,682,608 B2
(45) Date of Patent: *Mar. 23, 2010

(54) STABILIZED PREPARATIONS CONTAINING ANTIBODY

(75) Inventors: Tadao Yamazaki, Shizuoka (JP); Hiroko Konishi, Shizuoka (JP)

(73) Assignee: Chugai Seiyaku Kabushiki Kaisha, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 10/488,050

(22) PCT Filed: Aug. 29, 2002

(86) PCT No.: PCT/JP02/08732

§ 371 (c)(1),
(2), (4) Date: Feb. 27, 2004

(87) PCT Pub. No.: WO03/018056

PCT Pub. Date: Mar. 6, 2003

(65) Prior Publication Data

US 2004/0213785 A1 Oct. 28, 2004

(30) Foreign Application Priority Data

Aug. 29, 2001 (JP) .............................. 2001-258988

(51) Int. Cl.
*A61K 39/395* (2006.01)
(52) U.S. Cl. .................................. 424/130.1; 424/1.49
(58) Field of Classification Search ............... 424/133.1
See application file for complete search history.

(56) References Cited

U.S. PATENT DOCUMENTS

| 5,157,113 A | 10/1992 | Dove et al. |
| 6,171,586 B1 * | 1/2001 | Lam et al. ................. 424/130.1 |
| 2003/0092622 A1 * | 5/2003 | Sato et al. .................... 514/12 |

FOREIGN PATENT DOCUMENTS

| EP | 0 428 758 A1 | 5/1991 |
| EP | 0 852 951 A1 | 7/1998 |
| EP | 0 909 564 A1 | 4/1999 |
| EP | 1069185 | 1/2001 |
| JP | 02-000493 | 1/1990 |
| JP | 3-17023 A | 1/1991 |
| JP | 10-182481 A | 7/1998 |
| WO | WO-90/11091 | 10/1990 |
| WO | WO 99/10011 | 3/1999 |
| WO | WO-01/64241 | 9/2001 |

OTHER PUBLICATIONS

Kuby, Immunology, 1992, p. 124.*
Tsutomu Arakawa et al, "Stabilizing Effects of Caprylate and Acetyltryptophanate on Heat-Induced Aggregation of Bovine Serum Albumin", Biochimica et Biophysica Acta, 2000, vol. 1479, pp. 32-36.
Luciano Saso et al, "Effect of Selected Substances on Heat-Induced Aggregation of Albumin, IGG and Lysozyme", Research Communications in Molecular Pathology and Pharmacology, Oct. 1998, vol. 102, pp. 15-28.
A. Shrake et al, "Thermal Stability of Human Albumin Measured by Differential Scanning Calorimetry", I. Effects of Caprylate and N-Acetyltryptophanate, 1984, vol. 47, pp. 7-18.
P.D. Ross et al, "Thermal Stability of Human Albumin Measured by Differential Scanning Calorimetry", II. Effects of Isomers of N-Acetyltryptophanate and Tryptophanate, pH, Reheating, and Dimerization, 1984, vol. 47, pp. 19-27.
M.W. Yu et al, "Stabilization of Human Albumin by Caprylate and Acetyltryptophanate", 1984, vol. 47, pp. 28-40.
Paul D. Boyer et al, "The Combination of Fatty Acids and Related Compounds With Serum Albumin", I. Stabilization Against Heat Denaturation, Oct. 6, 1945, vol. 162, pp. 181-198.

* cited by examiner

*Primary Examiner*—Michael Szperka
*Assistant Examiner*—Yunsoo Kim
(74) *Attorney, Agent, or Firm*—Browdy and Neimark, PLLC

(57) ABSTRACT

A stabilized antibody-containing preparation containing acetyltryptophan or an acetyltryptophan derivative or a salt thereof as a stabilizer for controlling the decrease in the biological activity of the antibody.

9 Claims, No Drawings

STABILIZED PREPARATIONS CONTAINING ANTIBODY

TECHNICAL FIELD

The present invention relates to antibody-containing preparations, particularly stabilized antibody-containing preparations in which the biological activity of the antibody is not damaged even after long-term storage.

BACKGROUND ART

With the development of genetic engineering technology, various protein formulations became supplied in stable amounts. To ensure stability, these formulations are supplied in the dosage form of a lyophilized protein ingredient powder to be dissolved just before use in a separately packaged water-soluble diluent or in the dosage form of a protein solution formulation containing additives for improving stability.

Recently, efforts have been made to provide various antibody preparations in the form of solution formulations, but antibodies such as immunoglobulins, monoclonal antibodies and humanized antibodies are unstable proteins liable to physical or chemical changes such as association or aggregation under stresses of filtration, concentration and heating for removing viruses during the purification step. Antibody preparations also have the disadvantage that the biological activity of the antibodies decreases after long-term storage though it is essential for them to maintain the binding activity for their antigens in vivo.

A stabilization effect was found by adding polymers including proteins such as human serum albumin or purified gelatin or oligomers such as polyols, amino acids and surfactants as stabilizers for controlling chemical or physical changes. However, the addition of proteins such as human serum albumin or purified gelatin as stabilizers involves a very complicated step for removing viral contamination or other problems.

Acetyltryptophan was added to proteins such as albumin, human growth hormones and human B cell differentiation factor (BCDF) (JPB No. HEI7-68137, JPA No. HEI10-265404, JPA No. HEI3-27320). We previously reported stabilizing hematopoietic growth factors such as G-CSF and EPO by adding acetyltryptophan (PCT/JP01/01524).

However, it has not been so far known to stabilize antibody preparations by adding acetyltryptophan. Moreover, all the conventional preparations stabilized with acetyltryptophan described above were reported to show improved protein residuals by adding acetyltryptophan, but its effect on controlling the decrease in the biological activity in protein preparations, especially antibody preparations has not been known.

DISCLOSURE OF THE INVENTION

An object of the present invention is to provide stable antibody preparations in which high percentages of the antibody residual and the biological activity of the antibody is highly maintained even after long-term storage.

As a result of careful studies to attain the above object, we accomplished the present invention on the basis of the finding that preparations in which high percentages of the antibody residual and the biological activity of the antibody is highly maintained even after long-term storage can be obtained by adding acetyltryptophan or an acetyltryptophan derivative or a salt thereof as a stabilizer.

Accordingly, the present invention provides a stabilized antibody-containing preparation containing acetyltryptophan or an acetyltryptophan derivative or a salt thereof as a stabilizer for controlling the decrease in the biological activity of the antibody.

The present invention also provides a method for controlling the decrease in the biological activity of the antibody in an antibody-containing preparation, comprising adding acetyltryptophan or an acetyltryptophan derivative or a salt thereof.

The present invention also provides a method for using acetyltryptophan or an acetyltryptophan derivative or a salt thereof for controlling the decrease in the biological activity of the antibody in an antibody-containing preparation.

THE MOST PREFERRED EMBODIMENTS OF THE INVENTION

Antibodies used in the present invention are not specifically limited so far as they bind to a desired antigen, and mouse antibodies, rat antibodies, rabbit antibodies, sheep antibodies, chimeric antibodies, humanized antibodies, human antibodies and the like can be used as appropriate. The antibodies may be polyclonal or monoclonal, but preferably monoclonal because homogeneous antibodies can be stably produced. Polyclonal and monoclonal antibodies can be prepared by processes well known to those skilled in the art.

Hybridomas producing monoclonal antibodies can be basically constructed by known techniques as follows. A desired antigen or a cell expressing a desired antigen is used as an immunizing antigen to immunize host cells according to a standard immunization technique, and the resulting immunized cells are fused to known parent cells by a standard cell fusion technique, and then the fused cells are screened for monoclonal antibody-producing cells (hybridomas) by a standard screening method. Construction of hybridomas can be performed according to the method of e.g. Milstein et al. (Kohler. G. and Milstein, C., Methods Enzymol. (1981) 73: 3-46). If the antigen has low immunogenicity, it can be bound to an immunogenic macromolecule such as albumin and used for immunization.

Recombinant antibodies can be used, which are produced by transforming a host with a suitable vector containing an antibody gene cloned from a hybridoma using genetic engineering techniques (for example, see Carl, A. K. Borrebaeck, James, W. Larrick, THERAPEUTIC MONOCLONAL ANTIBODIES, Published in the United Kingdom by MACMILLAN PUBLISHERS LTD, 1990). Specifically, the cDNA sequences for the variable regions (V regions) of an antibody are synthesized from mRNA of a hybridoma using a reverse transcriptase. Thus obtained DNA sequences encoding the V regions of the antibody of interest are linked to the DNA sequences encoding the constant regions (C regions) of the antibody of interest and integrated into an expression vector. Alternatively, the DNA sequences encoding the V regions of the antibody can be integrated into an expression vector containing the DNA sequences for the C regions of the antibody. They are integrated into the expression vector in such a manner that they can be expressed under the control of regulatory regions such as enhancers and promoters. Then, a host cell can be transformed with this expression vector to express the antibody.

In the present invention, recombinant antibodies, i.e. antibodies artificially modified to reduce antigenicity in humans or to attain other purposes, such as chimeric antibodies and humanized antibodies can be used. These modified antibodies can be prepared by known processes. Chimeric antibodies consist of the heavy and light chain variable regions of an antibody from a non-human mammal such as a mouse and the heavy and light chain constant regions of a human antibody and can be obtained by linking the DNA sequences encoding the variable regions of the mouse antibody to the DNA sequences for the constant regions of the human antibody and transforming a host with an expression vector containing the linked sequences to allow it to produce a chimeric antibody.

Humanized antibodies are also called reshaped human antibodies and obtained by grafting the complementarity-determining regions (CDRs) of an antibody from a non-human mammal such as a mouse into the complementarity-determining regions of a human antibody and typical gene recombination techniques for preparing them are also known. Specifically, DNA sequences designed to link the CDRs of a mouse antibody to the framework regions (FRs) of a human antibody are synthesized by PCR from several oligonucleotides prepared to have terminal overlapping regions. The resulting DNA sequences are linked to the DNA sequences encoding the constant regions of the human antibody and then integrated into an expression vector, which is transformed into a host to allow it to produce a reshaped antibody (see European Patent Publication No. EP 239400, International Publication No. WO 96/02576). The FRs of the human antibody linked by the CDRs are selected in such a manner that the complementarity-determining regions form an appropriate antigen-binding site. If necessary, reshaped humanized antibodies may have some amino acid changes in the framework regions of the variable regions so that the complementarity-determining regions form an appropriate antigen-binding site (Sato, K. et al., Cancer Res. (1993) 53, 851-856).

Methods for obtaining human antibodies are also known. For example, a desired human antibody having a binding activity for a desired antigen can be obtained by in vitro immunizing human lymphocytes with the desired antigen or a cell expressing the desired antigen and fusing the immunized lymphocytes to human myeloma cells such as U266 (see JPB No. HEI1-59878). A desired human antibody can also be obtained by immunizing a transgenic animal having all human antibody gene repertoires with an antigen (see International Publications Nos. WO 93/12227, WO 92/03918, WO 94/02602, WO 94/25585, WO 96/34096, WO 96/33735). Methods for obtaining a human antibody by panning using a human antibody library are also known. For example, phages binding to an antigen can be selected by expressing the variable regions of a human antibody as single chain antibody fragments (scFv) on phage surfaces by a phage display method. The DNA sequences encoding the variable regions of the human antibody binding to the antigen can be determined by analyzing the genes of the selected phages. A whole human antibody can be obtained by preparing a suitable expression vector on the basis of the determined DNA sequences of the scFv fragments binding to the antigen. These methods have already been well known from WO 92/01047, WO 92/20791, WO 93/06213, WO 93/11236, WO 93/19172, WO 95/01438, WO 95/15388.

When an antibody is to be prepared by transforming a preliminarily isolated antibody gene into a suitable host, the suitable host can be used in combination with an expression vector. Suitable eukaryotic cells used as hosts include animal and plant cells and fungi. Known animal cells include (1) mammal cells such as CHO, COS, myeloma, BHK (baby hamster kidney), HeLa and Vero cells; (2) amphibian cells such as Xenopus oocytes; or (3) insect cells such as sf9, sf21 and Tn5. Known plant cells include cells of *Nicotiana* such as *Nicotiana tabacum*, which can be used as callus cultures. Known fungi include yeasts such as *Saccharomyces* spp., e.g.

*Saccharomyces serevisiae* and filamentous fungi such as *Aspergillus* spp., e.g. *Aspergillus niger*. Prokaryotic cells can be used as producing systems using bacterial cells. Known bacterial cells include *E. coli* and *Bacillus subtilis*. Antibodies can be obtained by transforming these cells with an antibody gene of interest and culturing the transformed cells in vitro.

Not only the host cells described above but also transgenic animals can be used to produce recombinant antibodies. For example, an antibody gene is inserted into a gene encoding a protein produced specifically in milk (such as goat β casein) to prepare a fusion gene. A DNA fragment containing the fusion gene bearing the antibody gene is injected into the embryo of a goat and this embryo is implanted into a female goat. An antibody is obtained from the milk produced by transgenic goats born from the goat impregnated with the embryo or progeny thereof. To increase the amount of the antibody-containing milk produced by the transgenic goats, hormones may be administered to the transgenic goats as appropriate (see Ebert, K. M. et al., Bio/Technology (1994) 12, 699-702).

Antibodies contained in stabilized preparations of the present invention include, but not limited to, anti-tissue factor antibodies, anti-IL-6 receptor antibodies, anti-HM1.24 antigen monoclonal antibodies, anti-parathyroid hormone related peptide antibodies (anti-PTHrP antibodies), etc.

Preferred reshaped humanized antibodies are humanized anti-tissue factor antibodies (see International Publication No. WO99-51743). Other preferred antibodies for use in the present invention include humanized anti-IL-6 receptor antibodies (hPM-1) (see International Publication No. WO92-19759), humanized anti-HM1.24 antigen monoclonal antibodies (see International Publication No. WO98-14580) and humanized anti-parathyroid hormone related peptide antibodies (anti-PTHrP antibodies) (see International Publication No. WO98-13388).

Moreover, antibodies used in the present invention are not limited to whole molecule antibodies but may be antibody fragments or modified fragments and include divalent and monovalent antibodies so far as they bind to an antigen molecule to inhibit the activity of the antigen. For example, antibody fragments include Fab, (Fab')$_2$Fv, Fab/c having one Fab and a whole Fc, and single chain Fv (scFv) in which the heavy and light chain Fv fragments are joined with a suitable linker.

Specifically, an antibody is treated with an enzyme such as papain or pepsin to produce antibody fragments or the genes encoding these antibody fragments are constructed and introduced into an expression vector and then expressed in a suitable host cell (for example, see Co, M. S. et al., J. Imunol. (1994) 152, 2968-2976, Better, M. & Horwitz, A. H. Methods in Enzymology (1989) 178, 476-496, Academic Press, Inc., Plueckthun, A. & Skerra, A. Methods in Enzymology (1989) 178, 476-496, Academic Press, Inc., Lamoyi, E, Methods in Enzymology (1989) 121, 652-663, Rousseaux, J. et al, Methods in Enzymology (1989) 121, 663-669, Bird, R. E. et al., TIBTECH (1991) 9, 132-137).

Fragments scFv are obtained by joining the heavy chain variable region and the light chain variable region of an antibody. In the scFv fragments, the heavy chain variable region and the light chain variable region are joined by a linker, preferably a peptide linker (Huston, J. S. et al., Proc. Natl. Acad. Sci. U.S.A. (1988) 85, 5879-5883). The heavy chain variable region and the light chain variable region in the scFv fragments may be derived from any antibody described herein. The peptide linker used for joining the variable regions is e.g. a single-stranded peptide consisting of 12-19 amino acid residues.

The DNA sequences encoding the scFv fragments are obtained by PCR amplification using the entire sequences of the DNA encoding the heavy chain or the heavy chain variable region and the DNA encoding the light chain or the light chain variable region of the antibody or a part thereof encoding a desired amino acid sequence as templates in combination with primer pairs defining both ends of these sequences and then using the DNA encoding a peptide linker region in combination with a primer pair defining both ends thereof to be linked to the heavy and light chains.

Once the DNA sequences encoding the scFv fragments are prepared, an expression vector containing these fragments and a host transformed with the expression vector can be obtained by conventional methods, and the host can be used to give scFv by conventional methods.

These antibody fragments can be produced by the host after obtaining and expressing the genes for them in the same manner as described above. As used herein, the "antibody" also means to include these antibody fragments.

Modified antibodies including antibodies conjugated with various molecules such as polyethylene glycol (PEG) can also be used. As used herein, the "antibody" also means to include these modified antibodies. Such modified antibodies can be obtained by chemically modifying the antibodies obtained as above. Methods for modifying antibodies have already been established in this field of art.

Antibodies used in the present invention may also be bispecific antibodies. Bispecific antibodies may have antigen-binding sites recognizing different epitopes of an antigen molecule or may have one antigen-binding site recognizing an antigen molecule and another antigen-binding site recognizing a cytotoxin such as a chemotherapeutic agent or a cell-derived toxin. In this case, the cytotoxin can directly act on cells expressing the antigen molecule to specifically damage cancer cells so that the growth of the cancer cells can be inhibited. Bispecific antibodies can be prepared by joining HL pairs of two antibodies, or fusing hybridomas producing different monoclonal antibodies to prepare a fusion cell producing a bispecific antibody. Bispecific antibodies can also be prepared by genetic engineering techniques.

Antibodies contained in stabilized preparations of the present invention may belong to any immunoglobulin class, preferably IgG such as IgG1, IgG2, IgG3 and IgG4, more preferably IgG4.

As used herein, the antibody-containing sample may be a sample containing any antibody whether natural or recombinant, preferably a culture medium obtained after culturing antibody-containing mammalian cells such as CHO cells or further applying some treatment such as partial purification.

As used herein, the "biological activity of the antibody" means the binding activity of the antibody for its antigen or various biological activities generated by binding of the antibody to an antigen molecule such as neutralization activity, antagonist activity and agonist activity against the antigen molecule. The expression "controlling the decrease in the biological activity of the antibody" means maintaining 80% or more, preferably 90% or more of the biological activity of the antibody in the antibody formulation just prepared. The biological activity of the antibody can be determined by assays such as ELISA or using a surface plasmon sensor or the like.

Preferably, antibody preparations of the present invention are substantially free from proteins such as human serum albumin or purified gelatin as stabilizers.

Acetyltryptophan or acetyltryptophan derivatives or salts thereof used as stabilizers in the present invention include free acetyltryptophan or acetyltryptophan derivatives and salts thereof such as sodium salts, potassium salts and hydrochlorides. Acetyltryptophan or acetyltryptophan derivatives or salts thereof used in the preparations of the present invention may be D-, L- or DL-isomers, more preferably L-isomers. Acetyltryptophan derivatives include, but not limited to, acetyltryptophan methyl ester, acetyltryptophan ethyl ester, acetyltryptophan propyl ester, acetyltryptophan amide, chloroacetyltryptophan, etc.

The amount of acetyltryptophan or acetyltryptophan derivatives or salts thereof added to the preparations of the present invention depends on the nature and concentration of the antibodies used, dosage form (freeze-dried formulations or solution formulations) and the derivatives used. They are typically contained in freeze-dried formulations at a final dose of 0.1-300 mM, preferably 1-200 mM, more preferably 1-100 mM. They are typically contained in solution formulations at a final dose of 0.1-30 mM, preferably 0.5-20 mM, more preferably 0.5-10 mM. In the case of freeze-dried formulations, stable antibody preparations with excellent reconstitution can be provided at 0.1-30 mM, preferably 1-30 mM, more preferably 1-10 mM.

The weight ratio of antibodies to acetyltryptophan is generally 100:1-0.1:1. In the case of humanized anti-tissue factor antibodies, it is preferably 10:1-0.5:1, more preferably 2:1-1:1.

When the antibody is e.g. a humanized anti-tissue factor antibody, antibody preparations of the present invention show a residual of humanized anti-tissue factor antibody of 90% or more, preferably 95% or more and a residual of biological activity of 80% or more, preferably 90% or more after accelerated testing at 40° C. for 1 month.

Antibody preparations preferably have a pH of 4-8, more preferably 5-7.5. However, the pH depends on the antibody contained and is not limited to these values. In the case of e.g. humanized anti-tissue factor antibodies, the pH is preferably 4-7, more preferably 5-6. The pH can be adjusted with NaOH or the like, or basic amino acids such as histidine, arginine and lysine or basic amino acid derivatives or salts thereof to reduce antibody aggregation.

Preparations of the present invention may contain isotonizing agents, e.g., polyethylene glycol; and sugars such as dextran, mannitol, sorbitol, inositol, glucose, fructose, lactose, xylose, mannose, maltose, sucrose and raffinose.

Preparations of the present invention may further contain surfactants. Typical examples of surfactants include:

nonionic surfactants, e.g., sorbitan fatty acid esters such as sorbitan monocaprylate, sorbitan monolaurate, sorbitan monopalmitate; glycerin fatty acid esters such as glycerin monocaprylate, glycerin monomyristate, glycerin monostearate; polyglycerin fatty acid esters such as decaglyceryl monostearate, decaglyceryl distearate, decaglyceryl monolinoleate; polyoxyethylene sorbitan fatty acid esters such as polyoxyethylene sorbitan monolaurate, polyoxyethylene sorbitan monooleate, polyoxyethylene sorbitan monostearate, polyoxyethylene sorbitan monopalmitate, polyoxyethylene sorbitan trioleate, polyoxyethylene sorbitan tristearate; polyoxyethylene sorbitol fatty acid esters such as polyoxyethylene sorbitol tetrastearate, polyoxyethylene sorbitol tetraoleate; polyoxyethylene glycerin fatty acid esters such as polyoxyethylene glyceryl monostearate; polyethylene glycol fatty acid esters such as polyethylene glycol distearate; polyoxyethylene alkyl ethers such as polyoxyethylene lauryl ether; polyoxyethylene polyoxypropylene alkyl ethers such as polyoxyethylene polyoxypropylene glycol ether, polyoxyethylene polyoxypropylene propyl ether, polyoxyethylene polyoxypropylene cetyl ether; polyoxyethylene alkyl phenyl ethers such as polyoxyethylene nonyl phenyl ether; polyoxyethylene hardened castor oils such as polyoxyethylene castor oil, polyoxyethylene hardened castor oil (polyoxyethylene hydrogenated castor oil); polyoxyethylene beeswax derivatives such as polyoxyethylene sorbitol beeswax; polyoxyethylene lanolin derivatives such as polyoxyethylene lanolin; polyoxyethylene fatty acid amides such as polyoxyethylene stearic acid amide having an HLB of 6-18;

anionic surfactants, e.g., alkyl sulfates having a C10-18 alkyl group such as sodium cetyl sulfate, sodium lauryl sulfate, sodium oleyl sulfate; polyoxyethylene alkyl ether sulfates having an average EO mole number of 2-4 and a C10-18 alkyl group such as sodium polyoxyethylene lauryl sulfate; alkyl sulfosuccinic acid ester salts having a C8-18 alkyl group such as sodium laurylsulfosuccinate; and natural surfactants, e.g., lecithin; glycerophospholipids; sphingophospholipids such as sphingomyelin; sucrose fatty acid esters of C12-18 fatty acids. Preparations of the present invention can contain one or more of these surfactants in combination.

Preferred surfactants are polyoxyethylene sorbitan fatty acid esters, more preferably Polysorbates 20, 21, 40, 60, 65, 80, 81, 85, most preferably Polysorbates 20 and 80.

The amount of surfactants to be added to antibody preparations of the present invention is typically 0.0001-10% (w/v), preferably 0.001-5%, more preferably 0.005-3%.

Antibody preparations of the present invention may further contain diluents, solubilizing agents, excipients, pH-modifiers, soothing agents, buffers, sulfur-containing reducing agents, antioxidants or the like, if desired. For example, sulfur-containing reducing agents include N-acetylcysteine, N-acetylhomocysteine, thioctic acid, thiodiglycol, thioethanolamine, thioglycerol, thiosorbitol, thioglycolic acid and salts thereof, sodium thiosulfate, glutathione, and sulfhydryl-containing compounds such as thioalkanoic acid having 1 to 7 carbon atoms. Antioxidants include erythorbic acid, dibutylhydroxytoluene, butylhydroxyanisole, α-tocopherol, tocopherol acetate, L-ascorbic acid and salts thereof, L-ascorbyl palmitate, L-ascorbyl stearate, sodium bisulfite, sodium sulfite, triamyl gallate, propyl gallate or chelating agents such as disodium ethylenediamine tetraacetate (EDTA), sodium pyrophosphate and sodium metaphosphate. Other components commonly added may also be contained, e.g., inorganic salts such as sodium chloride, potassium chloride, calcium chloride, sodium phosphate, potassium phosphate and sodium bicarbonate; and organic salts such as sodium citrate, potassium citrate and sodium acetate.

Preparations of the present invention can be prepared by dissolving these components in an aqueous buffer known in the field of solution formulations such as a phosphate buffer (preferably sodium monohydrogen phosphate—sodium dihydrogen phosphate system) and/or a citrate buffer (preferably sodium citrate buffer) to prepare a solution formulation, or freeze-drying or spray-drying thus prepared solution formulation by standard procedures. In the case of solution preparations, antibodies are preferably dissolved in a glycine buffer and/or histidine buffer to inhibit heat-induced aggregation. Aggregation can be further inhibited by adding glycine and/or sucrose.

Stabilized antibody preparations of the present invention are normally administered via parenteral routes such as injection (e.g. subcutaneous, intravenous or intramuscular injection) or percutaneous, mucosal, nasal or pulmonary administration, but may also be orally administered.

Stabilized preparations of the present invention may be in the form of solution formulations or freeze-dried formulations to be dissolved/reconstituted before use. Suitable excipients for freeze-drying include sugar alcohols or sugars such as mannitol or glucose.

The amount of antibodies contained in preparations of the present invention depends on the type of the disease to be treated, the severity of the disease, the age of the patient and other factors, but generally corresponds to a final concentration of 0.1-200 mg/ml, preferably 1-120 mg/ml.

The following examples further illustrate the present invention without, however, limiting the scope of the invention thereto. Various changes and modifications can be made by those skilled in the art on the basis of the description of the invention, and such changes and modifications are also included in the present invention.

EXAMPLES

Example 1

Effects of Acetyltryptophan on Residual of Humanized Anti-Tissue Factor Antibody and Biological Activity (1) Materials The humanized anti-tissue factor antibody is the humanized antibody prepared in Example 4 of International Publication No. WO99-51743 and belongs to immunoglobulin class IgG4.

(2) Test Samples

Formulated solutions containing 2 mg/mL humanized anti-tissue factor antibody, 20 mmol/L sodium citrate buffer (pH 5), 10 mmol/L sodium chloride and 0, 1.25 or 2.5 mg/mL acetyltryptophan were prepared and aseptically filtered, and then a vial was aseptically packed with precisely 1 mL of each solution. The humanized anti-tissue factor antibody used was a recombinant humanized anti-tissue factor antibody obtained with CHO cells, and the acetyltryptophan added was an L-isomer.

Thus aseptically prepared solution formulations containing the humanized anti-tissue factor antibody were used as test samples after accelerated testing in an incubator at 40° C. for 1 month.

(3) Method for Determining the Antibody Content and Calculating the Antibody Residual.

The humanized anti-tissue factor antibody content in each sample was determined by gel permeation chromatography (GPC) using 10 mmol/L sodium phosphate buffer, pH6.8/150 mmol/L sodium chloride as a mobile phase at a flow rate of 0.7 mL/min on a column (TOSOH G3000SW$_{XL}$).

The humanized anti-tissue factor antibody content determined by this method was used to calculate the antibody residual (%) after accelerated testing according to the following equation.

$$\text{Antibody residual (\%)} = \frac{\text{(Humanized anti-tissue factor antibody content after acceleration for a given period)}}{\text{(Humanized anti-tissue factor antibody content in unaccelerated formulation)}} \times 100$$

(4) Assay Protocol for Measuring the Biological Activity of the Antibody

The biological activity of the humanized anti-tissue factor antibody was assayed as follows. The antigen against which the humanized anti-tissue factor antibody is directed is tissue factor which promotes coagulation in tissue fluid and which is also called blood coagulation factor III or tissue thromboplastin. Tissue factor is a cofactor for blood coagulation factor VII initiating extrinsic coagulation and forms a molecular complex with factor VII or activated factor VIIa to activate factor X and factor IX. Thus, the biological activity of the humanized anti-tissue factor antibody can be determined by reacting antibody samples with blood coagulation factors III, VIIa and X to produce factor Xa and cleaving the factor Xa by its substrate to measure the absorbance of the color developed.

Reagents

Thromborel S: supplied by Dade Behring (a reagent containing coagulation factor III).

Factor VIIa: supplied by CALBIOCHEM.

Factor X: supplied by Enzyme Research.

Chromogenic substrate Testzyme S-2222: supplied by Daiichi Pure Chemicals.

TBS: supplied by TAKARA.

$CaCl_2$: commercial grade.

BSA: supplied by Sigma.

Hexadimethrine bromide: supplied by Sigma.

EDTA: commercial grade.

Preparation of the Reagents

Thromborel S: Thromborel S (200 mg/vial) is dissolved in 4 mL/vial of Milli-Q water. The solution is dispensed into tubes at 100 μL/tube and then stored at −80° C. Before use, the frozen solution is thawed at room temperature and then heated at 37° C. for 15 minutes.

Factor VIIa (coagulation factor): prepared at 500 PEU/mL in Assay Buffer (hereinafter referred to as A.B.). The solution is dispensed into tubes at 20 μL/tube and then stored at −80° C.

Factor X (coagulation factor): prepared at 25 PEU/mL in A.B. The solution is dispensed into tubes at 100 μL/tube and then stored at −80° C.

Chromogenic substrate S-2222: dissolved in 17 mL of Milli-Q water and stored at 4° C.

EDTA: prepared at 500 mM in Milli-Q water.

Polybrene solution: Hexadimethrine bromide is dissolved at 0.6 mg/mL in Milli-Q water.

Preparation of the Buffer and Solutions

Assay Buffer (A.B.): TBS (pH 7.6) containing 5 mM $CaCl_2$, 0.1% BSA.

Mixed solution of Factor VIIa & Thromborel S: a solution of Factor VIIa and Thromborel S diluted in A.B. to final concentrations of 0.1 PEU/mL and 1:120 (v/v), respectively.

Factor X solution: a solution of Factor X diluted in A.B. to a final concentration of 0.25 PEU/mL.

100×standard solution: a solution of the humanized anti-tissue factor antibody prepared at 180 μg/mL in A.B.

100×sample solution: a solution of the humanized anti-tissue factor antibody in each sample prepared at 120 μg/mL in A.B.

Mixed chromogenic substrate S-2222 solution: prepared at a ratio of chromogenic substrate S-2222: polybrene solution=1:1.

Method

1. Dispense the mixed solution of factor VIIa & Thromborel S into a plate at 60 μL/well and allow the plate to stand at room temperature for 60 minutes.

2. Dilute each of 100×standard solution and 100×sample solution 100-fold in Factor X solution.

3. Further dilute the standard solution to 1800 ng/mL -356 ng/mL and the sample solution to 1200 ng/mL-533 ng/mL in Factor X solution at a concentration ratio between the diluted solutions of 1.5.

4. Dispense the diluted sample into the plate at 40 μL/well and allow the plate to stand for 30 minutes.

5. Stop the reaction by adding 10 μL/well of 500 mmol/L EDTA solution, and then dispense the mixed chromogenic substrate S-2222 solution into the plate at 50 μL/well and allow the plate to stand at room temperature for 60 minutes.

6. Measure the absorbance at 405 nm-655 nm.

(5) Results

The results are shown in Table 1.

TABLE 1

| Concentration of acetyltryptophan | Antibody residual after 1 month @ 40° C. [% of Initial] | |
|---|---|---|
| [mg/mL] | GPC | Biological activity |
| 0 | 97.9 | 82.0 |
| 1.25 (5 mM) | 99.1 | 99.0 |

As shown from Table 1, the sample containing acetyltryptophan showed a remarkable stabilization effect with little decrease in biological activity while maintaining a high residual of antibody.

The invention claimed is:

1. A stabilized antibody-containing preparation containing an antibody and acetyltryptophan or an acetyltryptophan derivative or a salt thereof as a stabilizer capable of controlling the decrease in the biological activity of the antibody, wherein the antibody belongs to immunoglobulin class IgG and the preparation is substantially free from proteins as stabilizers.

2. The stabilized antibody-containing preparation of claim 1 wherein the stabilizer is acetyltryptophan or a salt thereof.

3. The stabilized antibody-containing preparation of claim 1 wherein the antibody is a chimeric antibody, humanized antibody or human antibody.

4. The stabilized antibody-containing preparation of claim 1 wherein the antibody is an antibody fragment, modified antibody or modified antibody fragment.

5. The stabilized antibody-containing preparation of claim 1 wherein the antibody is an anti-tissue factor antibody.

6. The stabilized antibody-containing preparation of claim 1 wherein the antibody is an anti-tissue factor antibody and the anti-tissue factor antibody is a humanized anti-tissue factor antibody.

7. The stabilized antibody-containing preparation of claim 1 in the form of a freeze-dried formulation.

8. The stabilized antibody-containing preparation of claim 1 in the form of a solution formulation.

9. The stabilized antibody-containing preparation of claim 1 wherein acetyltryptophan or an acetyltryptophan derivative or a salt thereof is contained at 1-100 mM.

* * * * *